United States Patent [19]

Litchfield et al.

[11] 4,327,181

[45] Apr. 27, 1982

[54] AEROBIC SUBMERGED FERMENTATION OF SPORULATING, ECTOMYCORRHIZAL FUNGI

[75] Inventors: John H. Litchfield; William T. Lawhon, Jr., both of Worthington, Ohio

[73] Assignee: Battelle Development Corporation, Columbus, Ohio

[21] Appl. No.: 150,095

[22] Filed: May 15, 1980

[51] Int. Cl.³ .............................................. C12N 11/14
[52] U.S. Cl. .................................. 435/176; 435/242; 435/911
[58] Field of Search ............... 435/254, 911, 818, 242, 435/176

[56] References Cited

U.S. PATENT DOCUMENTS 3,580,811  5/1971  Hidy ..................................... 435/911
4,051,314  9/1977  Ohtsuka et al. ...................... 435/911
4,162,939  7/1979  Yoshikumi ........................... 435/911
4,237,233  12/1980  Yoshikumi et al. ................. 435/254

FOREIGN PATENT DOCUMENTS 2032456  5/1980  United Kingdom ................ 435/254

OTHER PUBLICATIONS

Microbial Processes: Promising Technologies for Developing Countries, National Academy of Sciences 1979, Chap. 3, Soil Sii. Soc. Am. T., v 42, p. 906, (1978).

Primary Examiner—Hiram Bernstein
Attorney, Agent, or Firm—Barry S. Bissell

[57] ABSTRACT

Cultures of *Pisolithus tinctorius* and *Thelephora terrestris* can be grown by aerobic submerged fermentation in modified Pridham-Gottlieb medium at about pH 4–7 on a vermiculite carrier.

5 Claims, No Drawings

AEROBIC SUBMERGED FERMENTATION OF SPORULATING, ECTOMYCORRHIZAL FUNGI

BACKGROUND OF THE INVENTION

The symbiotic plant structures called mycorrhizae are formed when certain nutritionally exacting fungi become integrally associated with plant roots. Rather than acting pathogenically, these fungi enhance the growth of the infected plant by the increased uptake of nutrients and water and by the production of growth factors essential for higher plants. Mycorrhizal fungi, in return, utilize plant carbohydrates as a source of energy for metabolic processes.

Ectotropic mycorrhizal (ectomycorrhizal) fungi are important components of forest ecosystems in which the fungi infect the roots of pines and other trees in this symbiotic manner to enhance tree survival and growth, even in distressed soils. An example of the beneficial aspects of mycorrhizal fungi has been described by Marx (*The Ohio Journal of Science,* v. 75, no. 6, pgs. 288-297, 1975) in his attempts to increase pine seedling survival on spoiled lands. Marx reported a 35 percent increase in survival of pine seedlings specifically inoculated with a mycorrhizal fungus, *Pisolithus tinctorius,* compared to uninoculated seedlings. Unfortunately, the procedures described by Marx for cultivating mycorrhizal fungi on solid media are very time consuming and do not lend themselves to a large-scale production.

Other literature references to growth of mycorrhizal fungi can be found in: Ruehle and Marx, "Fiber, Food, Fuel and Fungal Symbionts", *Science,* v. 206, pgs. 419-422 (Oct. 26, 1979); Santoro and Casida, "Improved Method for Obtaining Vegetative Growth of Mycorrhizal and other Slow Growing Fungi", *J. Bacteriology,* v. 78, pgs. 449-450 (1959); van Eybergen and Scheffers, "Growth of the Mycelium of *Boletus edulis* on Agar Media and in Submerged Liquid Cultures", *Antonie van Leeuwenhock,* v. 38, pgs. 448-450 (1972). These publications generally disclose liquid cultures of species of *Boletus* and *Cenococcum,* which are non-sporulating, ectomycorrizal fungi, but they do not disclose the mass production of the specific sporulating organisms of the present invention.

The present invention is directed toward the mass cultivation of sporulating, ectomycorrhizal fungi in liquid culture. Such a procedure permits the continual, large-scale production of mycorrhizal fungi, for example, in a chemostat-like device used for continual liquid culture of bacteria. Such large-scale production is suitable for direct inoculation of tree roots or inoculation of soil prior to planting. In subcultural practices these techniques could lead to improvements in reclamation of strip-mined lands. In agricultural practices, inoculation with mycorrhizal fungi may lead to increased crop production with a decreased dependence on expensive, chemical fertilizers.

SUMMARY OF THE INVENTION

It is an object of the invention to provide a mycorrhizal fungal inoculum for forest tree roots to improve their growth and nutrient uptake.

It is further an object to provide such inoculum in large quantities.

It is therefore also an object to provide a method of mass producing mycorrhizal fungi especially in association with an inert carrier.

It is further an object to provide a method of mass production by submerged aerobic fermentation.

In accordance with the objectives, the invention is a method for mass producing mycorrhizal fungi and the fungi/carrier produced by the method which is useful in inoculating soil near tree roots. The method comprises inoculating a liquid growth medium with *Pisolithus tinctorius* or *Thelephora terrestris* and maintaining a pH therein at about 4.0-7.0 for a time sufficient to produce fungal growth.

The liquid growth medium typically comprises a composition containing sources of carbon and energy, nitrogen, vitamins and minerals. The fungi are preferably grown on an inert carrier which is suspended in the liquid growth medium and serves as a nucleation site. Particulate expanded minerals, such as vermiculite, are preferred.

The invention further comprises the mass inoculum consisting of the organisms *P. tinctorius* or *T. terrestris* in association with an inert carrier, such as the vermiculite, which is produced by the method and which can be turned into the soil near the roots.

DESCRIPTION OF THE INVENTION

Mycorrhizae are symbiotic, non-pathogenic associations of fungi and roots of plants. Virtually all higher plants form mycorrhizae. Ectotropic mycorrhizae are formed when surface fungus penetrates a root between cortical cells. These ectomycorrhizae are beneficial to tree roots by increasing their growth and nutrient uptake. Introduction of mycorrhizal fungi into the soil adjacent to tree roots can speed the process of forming the ectomycorrhizae and therefore promote increased tree survival and growth.

The problem in the past has been the ability to mass produce ectomycorrhizal fungi, and in particular, sporulating ectomycorrhizal fungi in sufficient quantity to supply large acreage of forest trees. Growth of these fungi has been suggested in the past on agar (solid media) but growth rates are very slow due to the small surface area.

Submerged aereated or aerobic fermentation is a known method for culturing organisms and would be useful in mass producing ectomycorrhizal fungi if feasible. Unfortunately, until the present invention, no submerged aerobic fermentation method existed for sporulating fungi. Sporulating fungi are obviously desirable because the spores are capable of growing directly into a new organism and can be transported in the soil by, for example, water flow, to infect more tree roots.

The organisms of the present invention which we have discovered can be cultured by submerged aerobic fermentation are *Pisolithus tinctorius* and *Thelephora terrestris.* These organisms are both of the class Basidiomycetes. *P. tinctorius* is of the subclass Homobasidiomycetidae and the order Sclerodermatales. *T. terrestris* is of the subclass Heterobasidiomycetidae and the order Thelephoraceae.

Some 73 forest species in 33 countries are infected by *P. tinctorius.* A list of the more important United States species includes:
1. Eucalyptus gummifera (Eucalyptus)
2. Pinus taeda (loblolly pine)
3. Pinus virginiana (Virginia pina)
4. Pinus strobus L. (Eastern white pine)
5. Pinus elliottii Englem, var. elliottii (Slash pine)
6. Pinus clausa var. immuginata Ward. (Sand pine)
7. Tsuga heterophylla (hemlock)

Trees infected by *T. terrestris* include:
1. Pinus taeda L. (loblolly pine)
2. Pinus virginiana (Virginia pine)
3. Pinus ponderosa (Ponderosa pine)
4. Tsuga heterophylla (Hemlock)
5. Pseudotsuga menziesii (Douglas fir)

According to the method, *P. tinctorius* and *T. terrestris* are grown by submerged aerobic fermentation. Mycelium of the two fungi are introduced into a liquid growth medium and incubated for a period of time sufficient to produce fungal growth. In our trials, large fungal colonies were produced in about 30 days.

During the period of incubation, the temperature of the liquid media is preferably maintained in the range of 10°–40° C. The higher temperatures seem to produce more Pisolithus while the Thelephora grew better at the lower temperatures in the range.

The liquid media are also constantly agitated during incubation to aereate. Cultures with and without carriers or nucleating sites have been grown in liquid media but better growth has been produced with particulate carriers present. The carriers could also carry nutrient but are preferably inert. Expanded mineral compositions in particulate form are preferred, especially vermiculite, montmorillonite group minerals and perlite. The carriers are also convenient in that soil application is improved. The fungal cells may be freeze-dried alone or as part of a carrier system including the particulate expanded mineral and possibly some additional soil nutrient. Application of this cell matter, with or without carrier and nutrient, is accomplished by broadcasting over the soil surface near existing or proposed trees and turning into the soil. Water in the soil then activates the freeze-dried cells.

The liquid media are conventional for other microorganism growth. The pH, however, is controlled between about 4.0 and 7.0. The necessary elements of the media include sources or carbon and energy, nitrogen, vitamins and minerals.

The carbon/energy sources typically consist of simple sugars, such as glucose, sucrose, maltose, or raw materials containing these simple sugars, for example, corn syrup or beet, cane or sorghum juices or molasses.

The nitrogen sources comprise ammonium salts, nitrates and organic materials such as urea, casein hydrolysates (peptone), corn steep liquor or distillers solubles.

Vitamin sources include trace growth factors and are found in supplements such as yeast extract and corn steep liquor. Minerals such as potassium (both as a nutrient and pH buffer), magnesium, copper, iron, manganese and zinc are also necessary for growth.

A solid growth medium used in culturing fungi is known as Pridham-Gottlieb medium (MPG). A particularly preferred liquid growth medium used in practicing the invention is obtained by omitting agar from the modified Pridham-Gottlieb medium. It is an aqueous solution (MPG solution) comprising the following aggregation of materials:

| Component | Concentration (g/l) |
|---|---|
| $KH_2PO_4$ | 2.38 |
| $K_2HPO_4$ | 5.65 |
| $MgSO_4 \cdot 7H_2O$ | 1.00 |
| $CuSO_4 \cdot 5H_2O$ | 0.0064 |
| $FeSO_4 \cdot 7H_2O$ | 0.0011 |
| $MnCl_2 \cdot 4H_2O$ | 0.0019 |
| $ZnSO_4 \cdot 7H_2O$ | 0.0015 |
| $NH_4NO_3$ | 3.0 |
| peptone | 10.0 |
| yeast extract | 2.0 |
| dextrose | 30.0 |

An alternative aqueous medium, adjusted to pH 4.0–7.0 is as follows:

| Component | Concentration (g/l) |
|---|---|
| $(NH_4)HPO_4$ | 5.0 |
| $CaCO_3$ | 2.0 |
| corn steep liquor | 12.0 |
| dextrose | 30.0 |

EXAMPLES OF THE PREFERRED EMBODIMENTS

Example 1—Solid Culture

To obtain starter cells for liquid culture and to compare the growth rate on solid culture mycelia of *P. tinctorius* and *T. terrestris* were inoculated into a solid nutrient of MPG (thus containing 20 grams/liter agar). Several plates were inoculated to compare the effects of several variables, including pH, temperature and additives of malic and/or succinic acid. Plates at each condition, were duplicated and the results averaged in Tables 1 and 2. Temperatures of 25° C. and 37° C. and pH of 4.0 and 6.0 were investigated. Incubation lasted for 30 days.

TABLE I
COLONY DIAMETERS OF *P. TINCTORIUS*

| Solid Medium | @ 25 C (cm ± SD) | @ 37 C (cm ± SD) |
|---|---|---|
| MPG, pH 4.0 | NG (no growth) | NG |
| MPG, pH 6.0 | 1.50 ± 0.08 | 3.56 ± 0.11 |
| MPG, 10 ppm malate, pH 4.0 | NG | NG |
| MPG, 10 ppm malate, pH 6.0 | NG | 1.48 ± 0.11 |
| MPG, 10 ppm succinate, pH 4.0 | NG | NG |
| MPG, 10 ppm succinate, pH 6.0 | 1.24 ± 0.03 | NG |
| MPG, 5 ppm malate, 5 ppm succinate, pH 4.0 | 1.80 ± 0.80 | NG |
| MPG, 5 ppm malate, 5 ppm succinate, pH 6.0 | NG | 2.79 ± 2.23 |

TABLE 2
COLONY DIAMETERS OF *T. TERRESTRIS*

| Solid Medium | @ 25 C (cm ± SD) | @ 37 C (cm ± SD) |
|---|---|---|
| MPG, pH 4.0 | NG (no growth) | NG |
| MPG, pH 6.0 | NG | 0.94 ± 0.19 |
| MPG, 10 ppm malate, pH 4.0 | NG | NG |
| MPG, 10 ppm malate, pH 6.0 | 2.22 ± 0.13 | NG |
| MPG, 10 ppm succinate, pH 4.0 | NG | NG |
| MPG, 10 ppm succinate, pH 6.0 | 2.32 | NG |
| MPG, 5 ppm malate, 5 ppm succinate, pH 4.0 | NG | 0.90 ± 0.14 |
| MPG, 5 ppm malate, 5 ppm succinate, pH 6.0 | NG | 0.92 ± 0.16 |

All rates of growth were slow (the growth is no more than a few cells thick) but *P. tinctorius* grew better at 37° C. and at pH 6.0. The organic acids did not seem to have a beneficial effect. However, in a separate effort to increase stock, Pisolithus grew well on the solid medium plus 10 ppm malic acid at pH 4.0.

*T. terrestris* also grew slowly, with the better results at 25° C. and pH of 6.0. Organic acids seems to improve yields of this organism.

Example 2—Liquid Culture

Cells produced in Example 1 were used to inoculate MPG solution. *P. tinctorius* was incubated at 37° C. and *T. terrestris* at 25° C., both for 39 days. Organic acid additions and pH were varied as was the presence of particulate vermiculite. The vermiculite served as a nucleation site as well as a carrier for the complete growth.

Tables 3 and 4 show the growth of the fungal mycelia. Each set of conditions was reproduced in duplicate and the results averaged. Both species grew substantially faster in liquid culture with the *P. tinctorius* displaying the better growth rate. Vermiculite appeared to improve growth rate in all cases. Organic acid additions to the MPG solution did not beneficially affect growth of *P. tinctorius*. Growth of this organism did seem to be greater at pH 6.0 than at pH 4.0.

TABLE 3

DRY BIOMASS OF *P. TINCTORIUS* IN LIQUID CULTURE

| Medium | Carrier | biomass (mg ± SD) |
|---|---|---|
| MPG, pH 6.0 | none | 855.3 ± 13.1 |
| MPG, pH 6.0 | 3g. vermiculite | 1015.0 ± 66.8 |
| MPG, 10 ppm malate, pH 4.0 | none | 167.0 ± 9.9 |
| MPG, 10 ppm malate, pH 4.0 | 3g. vermiculite | 322.2 ± 41.4 |
| MPG, 10 ppm malate, pH 6.0 | none | 807.3 ± 106.0 |
| MPG, 10 ppm malate, pH 6.0 | 3g. vermiculite | 915.0 ± 63.6 |

TABLE 4

DRY BIOMASS OF *T. TERRESTRIS* IN LIQUID CULTURE

| Medium | Carrier | biomass (mg ± SD) |
|---|---|---|
| MPG, 10 ppm malate, pH 4.0 | none | 194.0 ± 22.6 |
| MPG, 10 ppm malate, pH 4.0 | 3g. vermiculite | 259.3 ± 104.0 |
| MPG, 10 PPM succinate, PH 6.0 | none | 138.5 ± 2.8 |
| MPG, 10 ppm succinate, pH 6.0 | 3g. vermiculite | 350.3 ± 73.2 |

Based on an original inoculum of 30 mg, the *P. tinctorius* multiplied between about 5 and 30 times whereas the *T. terrestris* increased between about 4 to 10 times.

Example 3—Liquid Culture

*P. tinctorius* and *T. terrestris* were inoculated onto plates of solid MPG to obtain enough inoculum for liquid culture. However, only Pisolithus produced enough growth in about one month for liquid culture inoculum.

0.061 grams of *P. tinctorius* cells were inoculated in each of the following media: (1) MPG solution, (2) MPG solution plus 10 ppm citric acid, (3) MPG solution plus 10 ppm fumaric acid. Each of these media was also inoculated at pH 4.0 and pH 6.0 and each pH condition was further duplicated with and without 3 gram additions of vermiculite. A control MPG solution was also used at both pH levels, with and without vermiculite, but all with no inoculum of *P. tinctorius*. None of these control cultures produced biomass. Finally, these conditions were all duplicated and in most cases, average results are reported. In some cases, where one culture produced large growth and the other produced no growth, we assumed a poor inoculation and discounted the no growth result. Table 5 shows the resulting growth.

TABLE 5

DRY BIOMASS OF *P. TINCTORIUS* IN LIQUID CULTURE

| Medium | pH | vermiculite carrier | Biomass (mg ± SD) |
|---|---|---|---|
| MPG + 10 ppm citric | 6.0 | No | 43 ± 25 mg |
| MPG + 10 ppm citric | 6.0 | Yes | 313 mg (1 sample) |
| MPG + 10 ppm citric | 4.0 | No | 0 |
| MPG + 10 ppm citric | 4.0 | Yes | 0 |
| MPG + 10 ppm fumaric | 6.0 | No | 106 ± 20 mg |
| MPG + 10 ppm fumaric | 6.0 | Yes | 237 ± 7.1 mg |
| MPG + 10 ppm fumaric | 4.0 | No | 3.0 ± 4.2 mg |
| MPG + 10 ppm fumaric | 4.0 | Yes | 15.8 (1 sample) |
| MPG | 6.0 | No | 233 ± 248 mg |
| MPG | 6.0 | Yes | 300 ± 192 mg |
| MPG | 4.0 | No | 0 |
| MPG | 4.0 | Yes | 157 (1 sample) |

Again the better growth occurred at the higher pH and with the vermiculite in the solution. Also, results obtained with additions of organic acids to the MPG solution were inclusive. However, growth under several of these conditions was very substantial and shows that mass production of these sporulating, ectomycorrhizal fungi can be accomplished in liquid culture for inoculation on tree roots and into forest soils. A continuous mass production process can easily be envisioned wherein liquid media is moved in countercurrent fashion to a carrier, such as the vermiculite, and is continuously replenished and inoculated with the *P. tinctorius* or *T. terrestris*. The carrier and fungal growth is thereafter recovered and freeze-dried, ready for dispersal in forest soil.

We claim:

1. A method for mass production of sporulating, ectomycorrhizal fungi comprising inoculating a liquid growth medium with Thelephora terrestris and cultivating by aerobic submerged fermentation at a pH of between about 4.0 and 7.0 for a time sufficient to produce fungal growth.

2. The submerged fermentation method of claim 1 wherein the liquid growth medium comprises a composition having sources of carbon and energy, nitrogen, vitamins and minerals.

3. The submerged fermentation method of claims 1 or 2 wherein an inert carrier is suspended in the liquid growth medium as a site for nucleating fungal growth.

4. The submerged fermentation method of claim 3 wherein the carrier is an expanded mineral.

5. The submerged fermentation method of claim 3 wherein the carrier is particulate vermiculite.

* * * * *